(12) United States Patent  (10) Patent No.: US 8,579,889 B2
Bencini  (45) Date of Patent: Nov. 12, 2013

(54) LINEAR ABLATION DEVICES AND METHODS OF USE

(75) Inventor: Robert F. Bencini, Sunnyvale, CA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 1130 days.

(21) Appl. No.: 12/351,060

(22) Filed: Jan. 9, 2009

(65) Prior Publication Data

US 2009/0182316 A1 Jul. 16, 2009

Related U.S. Application Data

(60) Provisional application No. 61/020,486, filed on Jan. 11, 2008.

(51) Int. Cl.
*A61B 18/18* (2006.01)
(52) U.S. Cl.
USPC .......................................................... 606/20
(58) Field of Classification Search
USPC ........... 604/20–26; 606/25, 23, 21, 26, 22, 20
See application file for complete search history.

(56) References Cited

U.S. PATENT DOCUMENTS

| 5,462,521 | A | 10/1995 | Brucker et al. |
| 5,868,735 | A | 2/1999 | Lafontaine |
| 6,517,533 | B1 | 2/2003 | Swaminathan |
| 6,537,271 | B1 | 3/2003 | Murray et al. |
| 6,575,966 | B2 | 6/2003 | Lane et al. |
| 6,602,242 | B1 | 8/2003 | Fung et al. |
| 6,796,979 | B2 | 9/2004 | Lentz |
| 6,811,550 | B2 | 11/2004 | Holland et al. |
| 2003/0088240 | A1* | 5/2003 | Saadat ............................ 606/21 |
| 2009/0287202 | A1* | 11/2009 | Ingle et al. ...................... 606/21 |

FOREIGN PATENT DOCUMENTS

| WO | WO 99/27862 | 6/1999 |
| WO | WO 01/64145 | 9/2001 |
| WO | WO 02/102234 | 12/2002 |
| WO | WO 03/039338 | 5/2003 |

* cited by examiner

*Primary Examiner* — Nicholas Lucchesi
*Assistant Examiner* — Pritesh Patel
(74) *Attorney, Agent, or Firm* — Faegre Baker Daniels LLP

(57) ABSTRACT

Described herein are various methods and devices for delivering cryoablative therapy. Various ablative patterns can be produced by the devices, including, linear ablation patterns. One exemplary device includes a cryoablation chamber and a volume displacement chamber. In use, the volume displacement chamber can be expanded to support the cryoablation chamber.

21 Claims, 5 Drawing Sheets

LINEAR ABLATION DEVICES AND METHODS OF USE

This application claims priority to Provisional Application Ser. No. 61/020,486 entitled "Linear Ablation Devices and Methods of Use" filed Jan. 11, 2008, which is incorporated herein by reference.

BACKGROUND

Atrial fibrillation is a common cardiac arrhythmia. Patient's suffering from atrial fibrillation experience malfunctions of their heart's electrical system that cause the atria to quiver rapidly instead of beating in a normal pattern. This quivering prevents the heart from properly pumping blood and can eventually lead to clot formation and stroke.

Treatments for atrial fibrillation include drug therapy, electrocardioversion, and surgical or intravascular ablation techniques. Surgical and catheter based techniques have grown in popularity because drug therapy may be ineffective in some patients, showing success rates as low as fifty percent. Along with this low success rate, drug therapies also have deleterious side effects.

Surgical ablation requires a more invasive procedure whereby the surgeon creates a maze-like pattern of incisions on the inside of the patient's atria. The scarring that results acts to block the abnormal electrical pathways in the heart that lead to atrial fibrillation. Surgical ablation has a much higher success rate than drug therapies and lacks the potential for side effects presented by drug treatment. However, highly invasive (e.g., open-chest) procedures can present substantial risks.

Catheter ablation techniques use a less invasive approach and create scar tissue via a transvenous approach. A catheter delivers energy or cools tissue to cause lesional scarring without opening a patient's chest.

While current treatments address atrial fibrillation, further advances in ablation devices and their methods of use would be beneficial.

SUMMARY

Described herein are methods and devices for providing cryoablative therapy. In one aspect, a cryoablative device includes a cryoablation chamber having a shape and size configured to produce a linear ablation pattern.

In one embodiment the cryoablative device includes an elongate catheter body and an expandable member. With the expandable body in a low profile configuration, the catheter body permits delivery of the expandable body via a vasculature pathway. With the expandable body in an expanded configuration the expandable body can substantially fill an anatomic chamber.

In one aspect, the expandable body includes an expandable cryochamber and an expandable volume displacement chamber. In use, the volume displacement chamber can occupy a non-therapeutic volume and reduce the amount of cryofluid required to ablate target tissue. In another aspect, the expandable body can include more than one cryochamber and/or volume displacement chamber. In still another aspect, the expandable body includes a stand-along cryochamber. Instead of relying on a volume displacement chamber to support, expand, and/or position the cryochamber, the cryochamber can be expanded independently.

The cryochamber can have various shapes and sized that produce a linear ablation pattern when positioned in proximity to target tissue. In one aspect, the cryochamber has an elongate shape when at least partly expanded. In another aspect, the cryochamber corresponds to at least a portion of a Cox-Maze pattern. In still another aspect, the cryochamber corresponds to at least a portion of a gate or block around a pulmonary vein or veins.

It is to be understood that both the foregoing general description and the following detailed description are exemplary and are not restrictive of the invention, as claimed.

BRIEF DESCRIPTION OF THE DRAWINGS

The accompanying drawings, which are incorporated in and constitute a part of this specification, illustrate exemplary embodiments of the invention and together with the description, serve to explain the principles of the invention.

DETAILED DESCRIPTION

Described herein are methods, devices, and systems for ablating tissue, and in particular, for ablating tissue with a cryofluid. In one embodiment, an expandable cryoablation device permits a user to form a linear ablation pattern. In another aspect, the cryoablation device is adapted for creating linear ablation patterns within or around cardiac anatomy. Methods for creating linear ablation patterns are also described herein.

Figure 1:
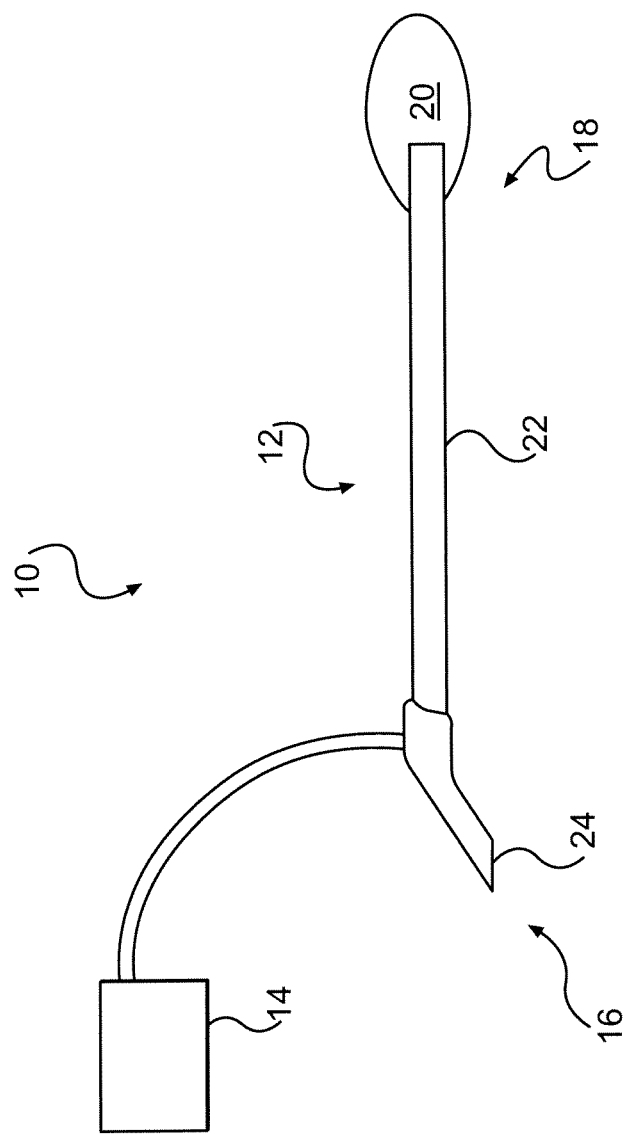
FIG. 1 is a side view of one exemplary embodiment of a cryoablation system described herein.

FIG. 1 illustrates one exemplary embodiment of a system 10 comprising an ablation device 12 and a source of fluid 14. In one aspect, device 12 includes an elongated body 22 extending between proximal and distal ends 16, 18. The distal end of device 12 can include an expandable body 20 for receiving cryofluid, as will be discussed in more detail below.

Proximal to expandable body 20, device 12 can include elongate body or shaft 22. In one aspect, shaft 22 is defined by a flexible or rigid body having one or more channels through which treatment fluids can be delivered. For example, shaft 22 can include at least one lumen for the delivery of a cryofluid and/or at least one lumen for the delivery of a volume displacement fluid. In addition, wires for conducting therapeutic energy and/or for sending/receiving sensed signals can extend along at least a portion of shaft 22. In one aspect, the wires connect a sensor or sensors positioned on, in, within expandable body 20 with a proximal processor and/or display. The sensors can permit, for example, cardiac mapping, temperature sensing, and/or pressure sensing.

The shaft can include a variety of features to facilitate insertion and/or placement of the expandable body relative to target tissue. In one embodiment, device 12 can include an articulating segment defined by a portion of shaft 22. For example, a distal portion of shaft 22 can be actuated by a user from a proximal location to steer expandable body into a target location. In one exemplary aspect, shaft 22 can include push and/or pull strands to transmit forces to the articulation segment.

The size and shape of shaft 22 can be chosen based on the intended use of device 12. Where device 12 is used for cardiac ablation, shaft 22 can be sized and shaped for insertion through a vascular lumen. In addition, the materials and structure of shaft 22 can be chosen to provide a flexible elongated body. One skilled in the art will appreciate that shaft 22 can represent the variety of catheter structures commonly known in the art for a vascular approach. However, the devices described herein need not be delivered via a transvenous route and/or the target tissue need not be cardiac tissue.

The proximal end of device 12 can include a user interface or handle 24 that permits a clinician to grasp device 12. Handle 24 can have a variety of forms depending on the intended use of device 12 and/or the environment in which device 12 is used. In one aspect, handle 24 can include one or more sources of liquid or gas for expanding expandable body 20. Controls for governing the delivery of liquid, such as a cryofluid or volume displacement fluid, can, in one aspect, also be located on handle 24. Alternatively, or additionally, handle 24 can be configured to mate with one or more sources of liquid such as fluid source 14. In one embodiment, source 14 includes a cryofluid and/or volume displacement fluid and can further include a mechanism for regulating and controlling expansion of expandable body 20 via delivery of fluid.

Figure 2A:
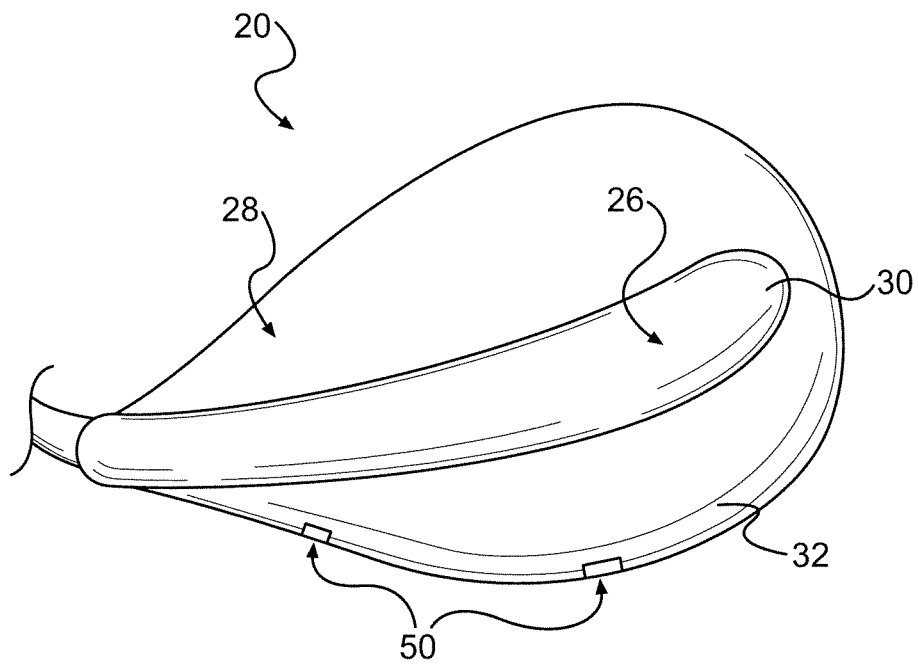
FIG. 2A is a side view of one exemplary embodiment of an expandable member described herein.
Figure 2B:
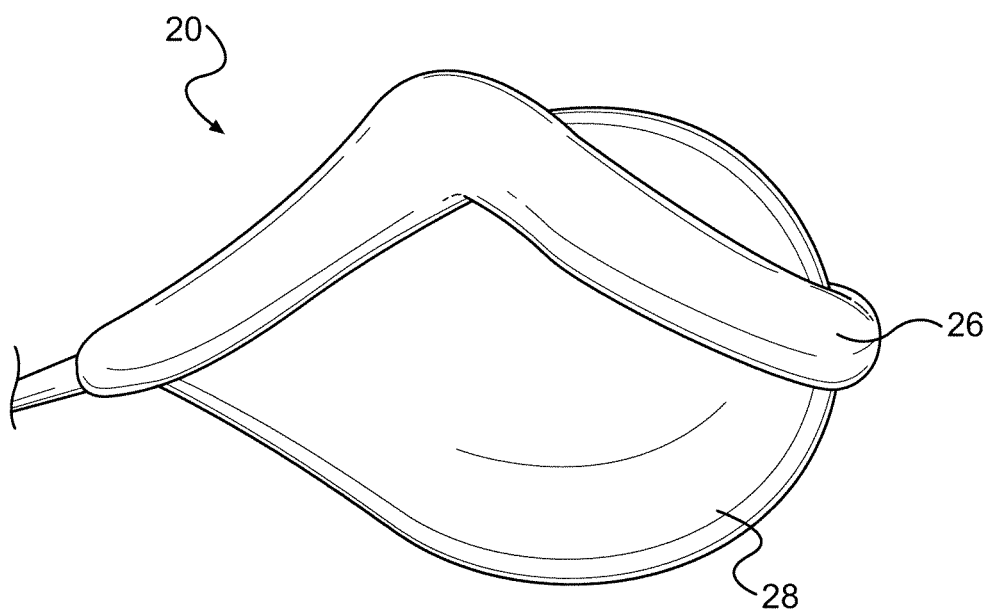
FIG. 2B is a side view of another exemplary embodiment of an expandable member described herein.

Returning to expandable body 20, FIGS. 2A and 2B illustrate a perspective view of the distal end of device 12 configured for providing a linear ablation pattern. As illustrated, expandable body 20 can comprise a first and a second chamber 26, 28. First chamber 26 can be a cryochamber configured to receive cryofluid and produce a linear ablation pattern. Second chamber 28 can be adapted to receive a fluid referred to herein as a volume expansion fluid. In one aspect, the volume expansion fluid is not a cryofluid. Instead, the volume expansion fluid can occupy a volume which supports the first chamber 26 and does not ablate tissue.

In one aspect, the linear pattern produced with expandable body 20 is a straight line. First chamber 26 can extend in a linear fashion when filled with cryofluid. Contacting tissue with expandable member 20, with cryofluid positioned within first chamber 26, creates a linear ablation pattern.

However, as used herein, the term "linear ablation pattern" can also refer an elongate, but not linear, shape. For example, expandable body 20 can be placed along a curved surface and produce an elongate ablation pattern that follows a curved or non-planar anatomic surface. Thus, in one aspect, the linear ablation pattern produced by device 12 is an elongate shape. In another aspect, the linear ablation pattern has a generally constant width and a length significantly greater than the width. In yet another aspect, the linear ablation pattern has a curved shape that extends substantially within a single plane. In still another aspect, the linear ablation pattern corresponds to a pattern that could be created by serially connecting a series of spot ablations.

Conventional radio frequency ablation tools can produce a spot lesion when placed in contact with tissue. In order to create a linear ablation pattern a series of adjoining ablation spots are formed. The device and methods disclosed herein allow a clinician to form a linear ablation pattern using cryoablation. In addition, a linear ablation pattern can be formed with fewer steps by delivering cryofluid to an elongate chamber.

In one embodiment, expandable member 20 forms a linear ablation pattern that blocks the passage of unwanted electrical signals. For example, the pattern can circumscribe the inside of an anatomic chamber or vessel. In another aspect, the linear ablation pattern can be sized and shaped to surround the opening of an anatomic vessel. For example, the cryoablation chamber can have an elongate shape that encircles a portion of expandable body 20 proximate to where the expandable body contacts target tissue.

In one embodiment, the cryochamber is positioned, sized, and shaped for creating linear ablation patterns in a cardiac chamber, such as, for example, the left and/or right atrium. In one aspect, the cryochamber is sized and shaped to form all or a portion of a box or gate lesion the encircles the left and/or right pulmonary vein. In another aspect, the cryochamber is sized and shaped to form a lesion corresponding to a incision or incisions that would be formed in the Cox-Maze procedure. In yet another aspect, the linear ablation pattern extends at least partially around the pulmonary veins (PV), left atrial appendage (LAA), left atrial isthmus (LAI), cavo-tricuspid isthmus (CTI), and/or intercaval lines (SIVC)

In another aspect, the cryochamber is not designed for creating the full or final ablation pattern in a single step. Instead, the cryochamber can form less than the desired ablation pattern. Moving the expandable member and/or the use of a second cryochamber permits formation of the desired ablation pattern.

Figure 3A:
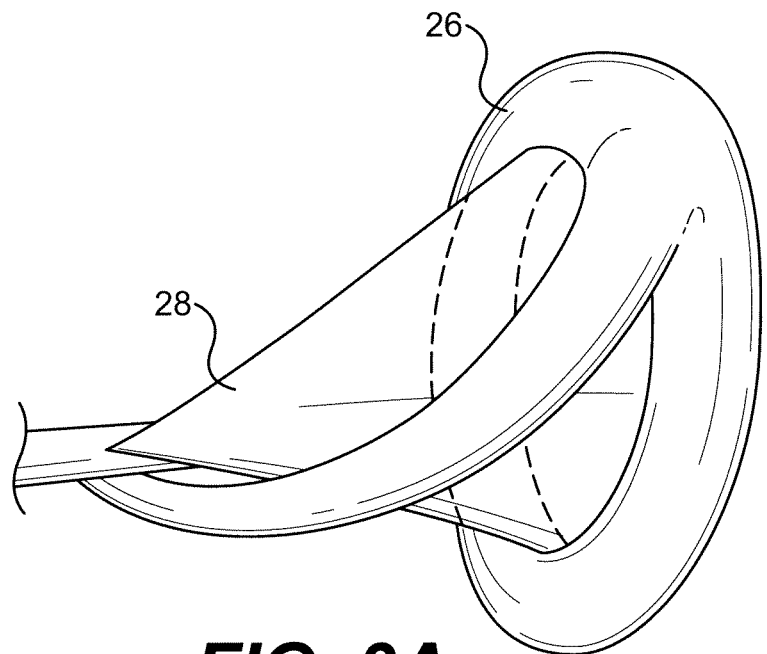
FIG. 3A is a perspective view of one exemplary embodiment of a cryochamber and volume displacement chamber described herein.
Figure 3B:
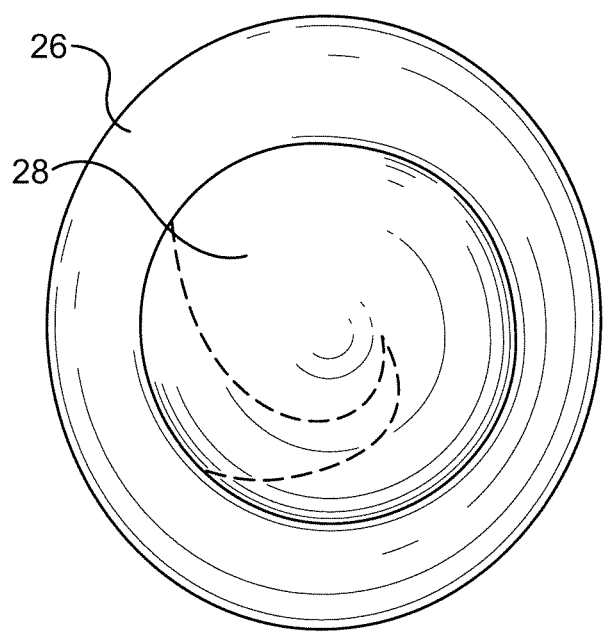
FIG. 3B is a front view of the cryochamber and volume displacement chamber of FIG. 3A.
Figure 4:
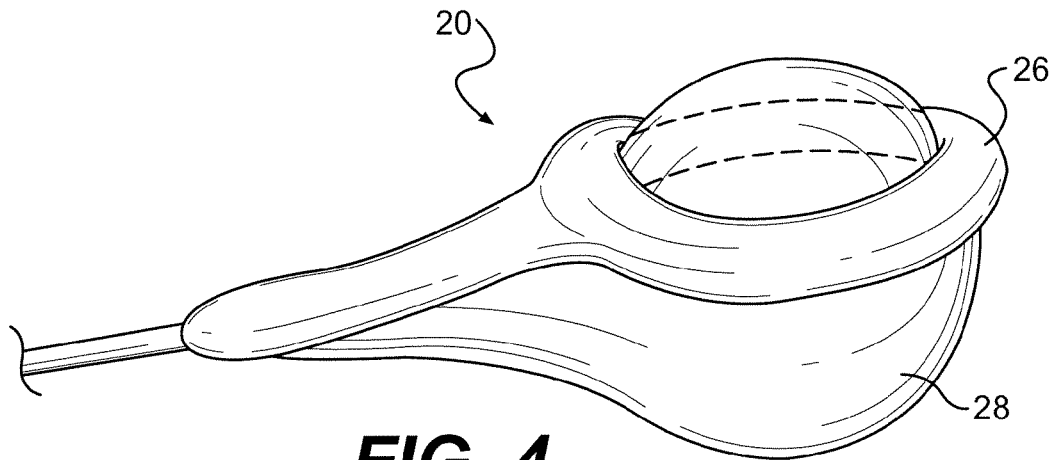
FIG. 4 is another exemplary embodiment of the device of FIG. 3A.

FIGS. 3A through 4 illustrate expandable body 20 with a cryochamber 26 configured for creation of a linear ablation pattern. In the illustrated embodiment cryochamber 26 has a generally circular configuration. However, cryochamber can have a variety of other shapes including rectangular, oval, triangular, irregular, etc. In one aspect, the cryochamber can have a size and shape corresponding to a tissue surface surrounding the pulmonary veins, a tissue surface defining an opening to the pulmonary veins, and/or a surface of the pulmonary vein/veins. The second chamber, which does not receive cryofluid, can correspond, at least in part, to the shape and/or size of an area which is not ablated, such as, for example, an open space (or non-tissue area) defined by the circumference of the vein/veins and/or a cardiac camber (e.g., right or left atria). In addition to these exemplary shapes and sized the cryochamber and volume displacement chamber can have a variety of alternative profiles for treating a variety of tissue surfaces including other cardiac tissue surfaces and/or non-cardiac tissue.

Figure 5:
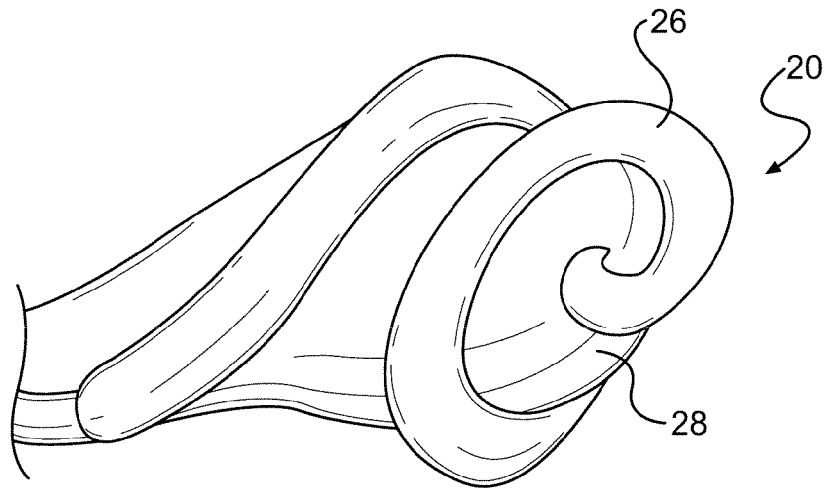
FIG. 5 is one exemplary embodiment of an expandable member described herein.

As an example of the various shapes of cryochamber 26, FIG. 5 illustrates a cork-screw configuration. In another aspect, the cryochamber could have a shape that corresponds to at least a portion of a Cox-Maze pattern.

The expandable body can fill a portion or all of an anatomic chamber when expanded. In one aspect, the portion of expandable body 20 defined by the volume expansion chamber 28 substantially fills an anatomic chamber. In the expanded stated the volume displacement chamber can support the cryochamber and/or inhibit unwanted movement of the cryochamber with respect to target tissue. For example, where the expandable body is positioned within the left or right atrium the volume expansion chamber can be expanded to substantially fill the left or right atrium. FIGS. 2A and 2B illustrate volume displacement chamber 28 expanded to substantially occupy an anatomic chamber. Before, during, and/or after expansion of the volume displacement chamber a user can adjust the position of the expandable body such that the volume expansion chamber is positioned adjacent to non-target tissue while the cryochamber is positioned adjacent to target tissue. Cryofluid can then be delivered to the cryochamber to ablate tissue. In one aspect, the volume displacement chamber does not completely fill an anatomic chamber and provides room for expansion of the cryochamber. In another aspect, expansion of the cryochamber displaces a portion of the volume displacement chamber.

In another embodiment, the volume displacement chamber 28 expands to support the cryochamber, but does not substantially fill an anatomic space. For example, in FIGS. 3A and 3B, the volume displacement chamber occupies space within cryochamber 26. Expansion of the volume displacement chamber can expand the outer surface of the cryochamber and hold the cryochamber against target tissue. However, the volume expansion chamber does not necessarily conform to adjacent tissue.

In yet another aspect, where the target tissue has a convex or protruding configuration, the expandable body can include a concave surface permitting receipt of tissue within a recess in the expandable body. The recess can assist with stabilizing the cryochamber with respect to target tissue. In one aspect, the volume displacement chamber includes a recessed surface. For example, the distal most surface of the volume displacement chamber 28 of FIG. 3B can have a concave shape.

A lumen extending from the proximal end of device 12 can deliver cryofluid to the cryochamber (first chamber 26). The proximal end of the lumen can include a fitting for mating with a source of cryofluid, particularly, with a source of pressurized gas or liquid. Conversely, the volume expansion chamber, second chamber 28, can be in fluid communication with a source of volume displacement fluid.

In one aspect, first chamber 26 extends across at least a portion of the second chamber and/or is positioned adjacent to the exterior of second chamber 28. In use, the first chamber can be located at least partially between target tissue and the second chamber. The relative location of the first and second chambers allow second chamber 28 to occupy a non-therapeutic volume of the expandable member. First chamber 26 can receive cooling fluid and cool target tissue positioned proximate to the first chamber while second chamber 28 can be expanded with a different fluid or higher temperature fluid.

Where the cryochamber 26 is positioned on, in, or along the outer surface of the volume displacement chamber, the cryochamber can occupy less than the full outer surface of the volume displacement chamber. In one aspect the cryochamber occupies less than about 70% of the surface area of the volume displacement chamber. In another aspect less than about 50%, less than about 30%, or less than about 20% of the surface area of the volume displacement chamber. In yet another aspect the cryochamber (or chambers) occupies about 5% to about 40% of the outer surface area of the volume displacement chamber.

When positioned within an anatomic structure, such as a vascular structure, expansion of second chamber 28 can assist with positioning and/or shaping first chamber 26. In a first aspect, second chamber 28 may apply pressure against first chamber 26. In this aspect, filling second chamber 28 with volume displacement fluid may act to move first chamber 26 towards or into contact with the target tissue. Additionally, or alternatively it may cause first chamber 26 to adopt a shape that partially conforms to that of the target tissue by pressing chamber 26 into the tissue. In another aspect, the force applied by second chamber 28 can cause tissue to deform into a desired shape.

Second chamber 28 can also assist with insulating non-target tissue. In this aspect, second chamber 28 may comprise a portion or portions of the first surface of expandable body 20, thereby excluding first chamber 26 from a portion or portions of the outer surface of expandable body 20. Tissue adjacent to or in contact with first chamber 26 can receive cryotreatment by being located near the cryofluid contained in first chamber 26. The tissue adjacent to or in contact with second chamber 28 can be insulated from the cryofluid contained in first chamber 26 by the fluid displacement fluid contained in second chamber 28, thereby avoiding cryotherapy treatment. Thus by locating second chamber 28 adjacent to or in contact with sensitive tissue, such as tissue not to be treated with cryotherapy or tissue previously treated with cryotherapy, the volume displacement chamber can protect such sensitive tissue.

In one embodiment, the first and second chambers are defined by first and second members 30, 32, respectively. In one aspect, first member 30 can be positioned on the outer surface of second member 32. Alternatively, or additionally, the first chamber can be at least partially recessed within the second chamber. Regardless, the shape and size of first member 30 can be chosen to produce the desired linear ablation pattern. For example, when expanded, first member 30 can have a shape that corresponds to the desired ablation pattern, such as, for example, a linear ablation pattern.

In one aspect, the shape of second member 32 facilitates proper positioning of the first member 30. A user can confirm the correct orientation of expandable body 20 by partly filling second member 32, aligning the shape of expandable member 20 with the surrounding anatomy, and then fully filling second member 32. With second member 32 in the proper position, the first member 30 will be positioned adjacent to the target tissue area. In addition, or alternatively, having second member 32 match the shape of a target anatomic site can reduce the chance of expandable member 20 shifting during use.

Thus, the first and/or second members 30, 32 can have a shape when expanded that matches an anatomic structure. Alternatively, the first and/or second member can flex, stretch, and/or deform such that the expandable body conforms to the surface of an anatomic structure. Thus, where the expandable body is used for different procedures and/or where the size of an anatomic structure varies from patient to patient, the properties of the expandable body can permit the expandable body to conform to the adjacent anatomy. Alternatively, the first and/or second chamber need not correspond to an anatomic shape and chambers 26 and 28 can have a variety of shapes including, for example, a cylindrical, spherical, conical or irregular shape.

In one aspect, first and second members 30, 32 can be expanded or inflated by stretching. Alternatively, the first and/or second member may be a non-stretchable, but flexible material. A member so constructed could expand by unfolding from an original collapsed and/or folded configuration. In another aspect, at least a portion of the first and/or second member can be deformable. Expansion can be achieved by deforming the walls of expandable member 20.

In one embodiment, first member 30 and second member 32 can have different properties. For example, first member 30 can have a higher thermal conductivity relative to the inner member to facilitate heat transfer between a cryofluid within the first chamber and adjacent target tissue. Conversely, second member 32 can have a lower thermal conductivity to limit the amount of heat transfer to the cryofluid within the first chamber and/or to inhibit freezing of the volume displacement fluid. A difference in the thermal conductivity can be achieved by using different materials, by using different material thicknesses, and/or by using an insulative layer.

In another aspect, expandable member can include materials for assisting with visualization. For example, at least a portion of the materials used to form expandable body 20 can be radio opaque. With respect to FIG. 2A, radio opaque markers 50 are incorporated into second member 32.

While the first and second members are described as being defined by distinct structures, one skilled in the art will appreciate that the first and second members can share a common wall. For example, the border between the first and second chambers can be defined by only a portion of the first or second members. Similarly, the first and second members can be formed of a unibody or single piece structure.

A variety of conventional cooling or cryofluids can be used with the devices described herein. The coolant fluid used to fill the first chamber 26 may be a liquid or a gas, or it may change phase from liquid to gas as it travels from the lumen through the first chamber 26. For example, the coolant may be a liquid with a low freezing point, such as saline, liquid nitrogen or other known heat transfer fluid. Alternatively, the coolant fluid may be a compressed fluid such as nitric oxide or other known refrigerant that expands as it enters the cooling chamber, thus decreasing the temperature of the first chamber 26 through the Joule-Thompson effect. In such instance, both the aerodynamics of the fluid's expansion and the final volume of the first chamber 26 after expansion can affect the final temperature of the coolant fluid.

The fluid used to fill the second chamber 28 can also have a cooling effect and/or can be chosen solely to occupy space and expand the second chamber. In one aspect, the volume displacement fluid is a biocompatible or medical grade fluid such as saline. In addition, the fluid may contain a contrast agent to aid in visualizing the cryotherapy device. In another aspect, the volume displacement fluid is chosen such that the volume displacement fluid does not freeze during cryotherapy treatment. One skilled in the art will appreciate that the volume displacement fluid can be selected depending on a variety of factors including the intended use of device 20, the configuration of the first and second chambers, the chosen cryofluid (e.g., cryofluid temperature), the volume displacement fluid freezing temperature, and/or thermal capacity.

Figure 6:
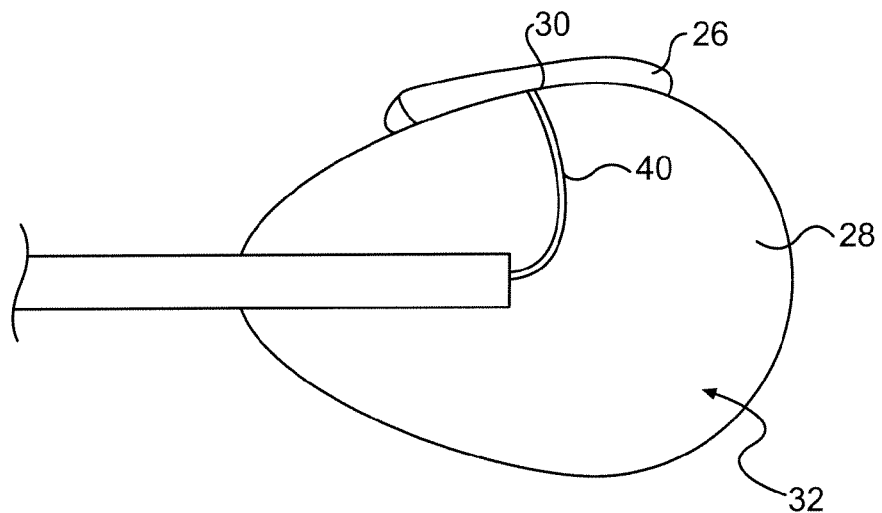
FIG. 6 is a cross-sectional view of a cryochamber and volume displacement chamber described herein.

In one embodiment, cryofluid travels through the second chamber to reach the first chamber. FIG. 6 is a cross-section of one embodiment of a cryotherapy device having within expandable body 20 first chamber 26, second chamber 28 and a pathway 40 extending through the second chamber 28. In one aspect, the pathway extends from the catheter shaft 22 through second chamber 28 and exits into the first chamber 26. While a single pathway is illustrated, pathway 40 may be branched, having multiple exit points into first chamber 26. Additionally, or alternatively, multiple pathways can extend to first chamber 26. Expandable body 20 can also include a spent coolant return lumen. For example, one or more exhaust or cool return lines (not illustrated) can extend from cryochamber 26 to shaft 22.

In use, routing pathway 40 through second chamber 28 can insulate cryofluid within pathway 40 from sensitive tissue and/or avoid inconsistent or localized cooling. Chamber 28 can space pathway 40 from the first walls of expandable member 20.

In another embodiment of device 12, instead of a second chamber moving (at least in part) a cryochamber into position, a device with a stand alone cryochamber is provided. Filling the cryochamber with cryofluid can move the expandable body into position for ablating tissue.

Figure 7A:
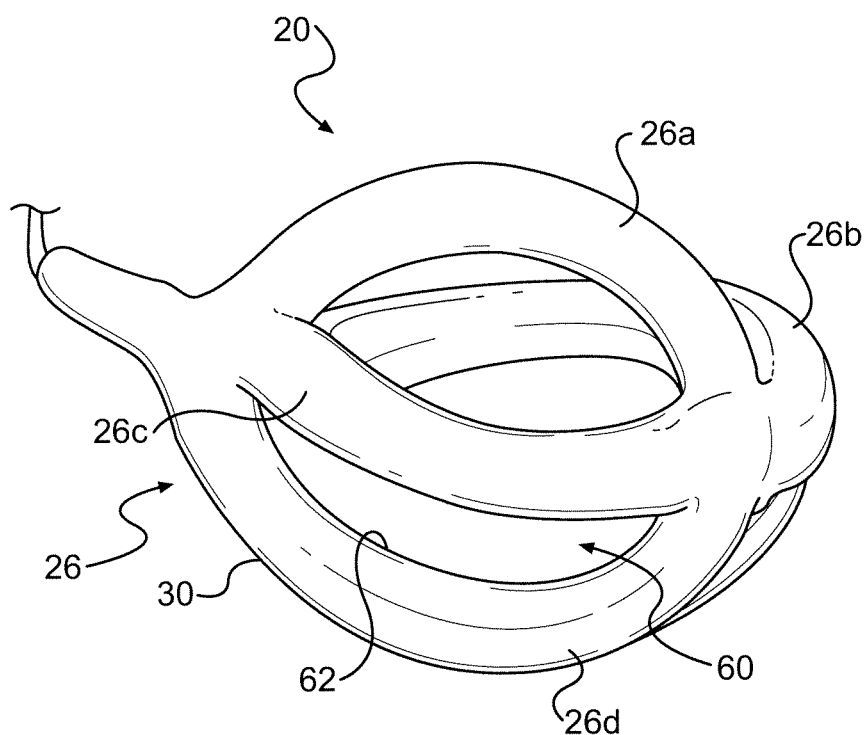
FIG. 7A is a perspective view of one exemplary embodiment of a stand-alone cryochamber described herein.
Figure 7B:
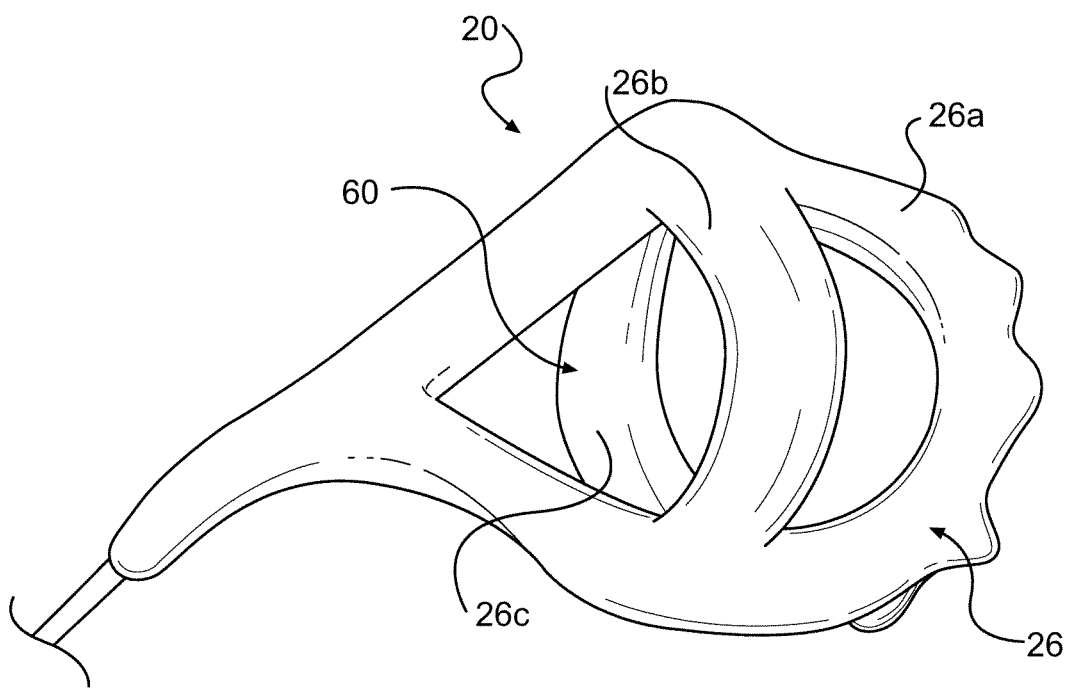
FIG. 7B is a perspective view of another exemplary embodiment of a stand-along cryochamber described herein.

With respect to FIGS. 7A and 7B, instead of second chamber 28 being positioned within first chamber 26, the area 60 within the first chamber can be an open or unoccupied space. Inflation of first chamber 26 causes the first chamber to move from a low profile, insertion configuration (not illustrated) to an expanded configuration for ablating tissue.

In one aspect, first chamber 26 can be comprised of multiple, spaced segments 26a, 26b, 26c, and/or 26d. A single coolant flow path can extend through one, two, or more of the segments such that coolant is delivered simultaneously. Alternatively, cryofluid flow through the segments can be individually controlled. In yet another aspect, one or more of the segments can receive volume displacement fluid in addition, or as an alternative to cryofluid.

In one embodiment central area 60 is exposed to the surrounding environment. The space between adjacent segments 26a, 26b, 26c, 26d of first chamber 26 can define at least one opening 62 into central area 60. The openings and/or open central region of expandable body 20 can permit the flow of blood through expandable member 20. Instead of blocking (or partially blocking) an anatomic vessel or chamber, the open area 60 within cryochamber 26 can permit blood flow during expansion and/or positioning of expandable body 20. Similarly, during ablation, device 12 can continue to permit blood flow.

In another embodiment, passages through the expandable body can be opened and closed to permit control of blood flow through expandable body 20. For example, blood flow can be interrupted during ablation. In one aspect, openings between segments 26a, 26b, etc. can be opened and closed. In another aspect a second member (not illustrated) can be expanded within area 60 to inhibit blood flow.

In an alternative embodiment area 60 can be enclosed. For example, a fluid impervious wall can extend between first chamber segments 26a, 26b, 26c, and/or 26d.

The cryochambers of FIGS. 7A and 7B can be expanded and/or reinforced in a variety of way in addition, or as alternative, to using cryofluid. In one aspect, a non-cryofluid is first delivered to expand cryochamber 26. Once the cryochamber is positioned and/or expanded, a cryofluid can be introduced into the cryochamber to ablate tissue. In another aspect, stiffening rods can be introduced into expandable member 20 to expand and/or reinforce cryochamber 26. In yet another aspect, a shape memory material or pre-bent material can be incorporated into expandable body 20. During insertion of expandable body 20 the material can be constrained. After positioning the expandable body in the desired location, the shape memory material or pre-bent material can cause the expandable body to expand.

Further described is an expandable body 20 with a protective layer. In any of the embodiments described herein, an additional expandable member can surround the first and/or second chambers. In one aspect, the protective layer can space the cryoablation chamber from target tissue to control or limit the amount of heat removed and/or the depth of ablation. The protective chamber can receive a source of volume displacement fluid that occupies an area between a surface of the first chamber 26 and target tissue. In addition, or alternatively, the protective chamber is not expanded or filled with fluid. Regardless, the protective layer can provide additional protection should one of the chambers rupture or break.

In one aspect, device 12 can incorporate or communicate with systems or devices for cardiac mapping. For example, expandable body 20 can incorporate sensors for sensing cardiac signals in adjacent tissue. Such sensors can be positioned on the outer surface of the expandable body and/or within (or inside) an outer layer of device 12 that permits sensing therethrough. In one exemplary aspect, sensors are mated with second chamber 28 and permit cardiac mapping.

Further described herein are methods of delivering cryoablative therapy. In one embodiment, expandable body 20 can be positioned adjacent to target tissue such as, for example, cardiac tissue. Once in position, the first and second chambers can be filled (or partially filled, or further filled) to position the cryochamber in position for delivery cryoablative therapy. In one aspect, cryofluid is delivered to the first chamber. For example, cryofluid can flow from a fluid source through catheter 22 and into the first chamber. A user or controller can regulate the delivery of cryofluid and/or volume displacement fluid to achieve the desired expansion. Alternatively, the expandable body 20 can be constrained to limit the maximum expansion of the first and/or second chambers. For example, the materials forming, incorporated into, and mated with the expandable body (e.g., first member 30, second member 32, and/or an outer protective layer) can limit the total expansion of the expandable body.

In one aspect, the expandable body 20 can be partially expanded by filling the second chamber 28 with fluid. Expandable body 20 can then be further expanded by filling the first chamber 26 with cooling fluid. In one aspect, first chamber 26 is expanded until expandable body 20 is in intimate contact with tissue to be treated. Expandable body 20 may remain in this expanded state for the time period required to ablate the tissue adjacent to the first chamber 26. Following this treatment period, cooling fluid can be removed from first chamber 26, and volume displacement fluid can be removed from second chamber 28.

Alternatively, after placement of expandable body 20 near the tissue to be treated, expandable body 20 can be partially expanded by first filling the first chamber 26 with cooling fluid. After filling the first chamber 26 with the desired amount of cooling fluid, expandable body 20 can be expanded in order to place the first chamber 26 adjacent to the tissue to be treated by filling the second chamber 28 with fluid. Expandable body 20 can remain in this expanded state for the time period required to ablate the tissue adjacent to the first chamber 26. Following the treatment period, cooling fluid can be removed from first chamber 26 and volume displacement fluid can be removed from second chamber 28.

A third method of using system 10 involves locating expandable body 20 near the tissue to be treated and first expanding expandable body 20 by filling the second chamber 28 with fluid until the second chamber 28 is adjacent to the tissue to be treated. At this point second chamber 28 accounts for most of the volume of expandable body 20. Next, cooling fluid is added to the first chamber 26 while at the same time fluid is removed from the second chamber 28 such that the overall volume of expandable body 20 remains substantially unchanged. This allows the first chamber 26 to expand into the region adjacent to the tissue to be treated and causes the second chamber 28 to be partially displaced away from the tissue to be treated. Following the treatment period the cooling fluid can be removed from the first chamber 26 and the fluid can be removed from the second chamber 28.

Other embodiments will be apparent to those skilled in the art from consideration of the specification and the disclosure therein. It is intended that the specification and examples be considered as exemplary only, with a true scope and spirit of the invention being indicated by the following claims.

What is claimed is:

1. A cryotherapy device comprising:
    an elongate catheter shaft extending between a proximal and distal end; and
    an expandable body comprising at least first and second cambers, the chambers positioned proximate to the distal end of the catheter shaft, the first chamber in fluid communication with a lumen for transmitting cryofluid to the first chamber, the first chamber having an elongate shape for creating a linear ablation pattern, the second chamber positioned adjacent to the first chamber,
    wherein the first chamber is positioned to deliver cryotherapy and form a linear ablation pattern when filled with cryofluid and wherein the second chamber is configured to support the first chamber.

2. The device of claim 1, wherein the second chamber has a size and shape, when expanded, that substantially corresponds to an anatomic structure.

3. The device of claim 1, wherein the second chamber is sized and shaped to occupy a cardiac chamber when expanded.

4. The device of claim 3, wherein the second chamber is configured to hold the first chamber in contact with tissue when expanded.

5. The device of claim 1, further comprising a source of cryofluid that is in fluid communication with the first chamber.

6. The device of claim 1, wherein the first chamber has a linear shape when expanded.

7. The device of claim 1, wherein the first chamber occupies less than about 50 percent of the surface area of the second chamber.

8. The device of claim 1, wherein the first chamber occupies less than about 30 percent of the surface area of the second chamber.

9. The device of claim 1, wherein the first chamber has a circular shape.

10. The device of claim 1, wherein the first chamber encircles, but does not enclose the second chamber.

11. The device of claim 1, wherein the first chamber encircles a non-ablating portion of the expandable body.

12. The device of claim 1, wherein the first chamber is adapted to form a lesion around at least a portion of a pulmonary vein.

13. The device of claim 1, further comprising an additional chamber for receiving cryofluid.

14. The device of claim 1, further comprising at least one radio opaque marker mated with the second chamber.

15. The device of claim 1, further comprising sensors for sensing cardiac signals.

16. The device of claim 1, wherein a first and second sensor are positioned on opposing sides of the first chamber for testing the ability of adjacent tissue to transmit electrical signals.

17. A cryotherapy device with stand-alone ablation chamber comprising:
    an elongate catheter shaft having a proximal and distal end;
    an expandable first chamber positioned proximate to the distal end of the catheter shaft, the first chamber in fluid communication with a lumen for transmitting cryofluid to the first chamber; and
    a source of cryofluid that is in fluid communication with the first chamber,
    wherein delivery of cryofluid to the first chamber cause the first chamber to move from a first, low profile delivery configuration to an expanded configuration such the first chamber is positioned for producing a linear ablation pattern.

18. The device of claim 17, further comprising a stiffening mechanism for supporting the first chamber.

19. The device of claim 18, wherein the catheter shaft includes a lumen for housing a stiffening rod.

20. The device of claim 17, wherein, when expanded, the first chamber defines an open interior region that is not in fluid communication with a source of fluid.

21. The device of claim 17, wherein at least a portion of the first chamber has a size and shape adapted to produce a linear ablation pattern when cryofluid is delivered into the first chamber.

\* \* \* \* \*